US005672517A

United States Patent [19]

Domingue

[11] Patent Number: 5,672,517
[45] Date of Patent: Sep. 30, 1997

[54] METHODS AND COMPOSITIONS FOR DIAGNOSIS AND TREATMENT OF INTERSTITIAL CYSTITIS

[76] Inventor: Gerald J. Domingue, 3540 Rue Michelle, New Orleans, La. 70131

[21] Appl. No.: 439,869

[22] Filed: May 12, 1995

[51] Int. Cl.$^6$ .................................................. G01N 33/557
[52] U.S. Cl. .................... 436/518; 435/7.24; 514/282; 514/560
[58] Field of Search .................... 435/7.24; 514/560, 514/282; 436/518

[56] References Cited

U.S. PATENT DOCUMENTS

| | | | |
|---|---|---|---|
| 5,158,870 | 10/1992 | Baseman | 435/7.32 |
| 5,196,514 | 3/1993 | Avakian et al. | 530/350 |
| 5,242,823 | 9/1993 | Fareed et al. | 435/252.3 |
| 5,369,005 | 11/1994 | Baseman | 435/6 |

OTHER PUBLICATIONS

Lind, K et al, J Clin Microbiolo, Dec. 1984, pp. 1036–1043, vol. 20(6).
Wein, AJ et al, Urol. Clin. North Am. (USA), 1994, 21(1), pp. 153–161.
Hanno, P.M., Urol. Clin. North Am. (USA) 1994, 21(1) pp. 63–66.
Trifillis, A.L et al, J. Urol, 1995, 153(1) pp. 243–248.
Mattila, J et al, Clin. Immunolo. Immunopathol., 1984, vol. 32(1), pp. 81–89.
MacDermott, JP et al, J. Urol, 1991 Feb., vol. 145(2) pp. 274–278.
Bullock, AD et al, J. Urol, 1992 Dec., vol. 148(6) pp. 1951–1956.
Warren, JW, Urol. Clin. North Am., 1994 Feb., vol. 21(1) pp. 31–39.
Baseman, J.B et al, Infect. Immunity, Mar. 1984, pp. 1103–1105, vol. 43(3).
Morrison–Plummer, J et al, Infect. Immunity, Jan. 1987, pp. 49–56, vol. 55(1).
Maniloff, J et al, "Mycoplasmas: Molecular Biology and Pathogenesis", 1992, pp. 32–40, 505–512, 417–444.
Felsen, D et al, J. Urol., 1994, vol. 152(2), pp. 355–361.
Stein, P.C. et al, J. Urol, 1993, vol. 150, pp. 1405–1408.
Ratliff, J.L. et al, Clin. Immunolo. Immunopath., vol. 74(3) Mar., pp. 209–216, 1995.
Sobeslavsky, O. et al, J Bacteriolo., 1968, pp. 695–705, vol. 96(3).
G.J. Domingue, "Cryptic bacterial genomes in interstital Cystitis," presented May 13, 1994 to Society for Basic Urologic Research.
G.J. Domingue, G.M. Ghoniem, L. G. Human, C. Fermin, and K. Johnston, Tulane University School of Medicine, New Orleans (Dr. Johnston is at LSU Medical Center), "Dormant Bacteria in Interstitial Cystitis," presented Jan. 9, 1995 to 1995 Interstitial Cystitis Scientific Research Symposium.
J. Nemec, "Have Bacteria been Overlooked in IC?" Urology Times/Sep. 1994, p. 13.
G.J. Domingue, K. Bost, G. Ghoniem, and L. Human, "Molecular Biology of Interstitial Cystitis", presented to American Society for Microbiology, abstract distributed May 15, 1994.
G.J. Domingue, R. Thomas, F. Walters, A. Serrano and P.M. Heidger, Jr. "Cell Wall Deficient Bacteria as a Cause of Idiopathic Hematuria," J. Urol. 150: 483–485 (1993).
G.J. Domingue, G.M. Ghoniem, K.L. Bost, C. Fermin, and Liset G. Human, "Dormant Microbes in Interstitial Cystitis, Journal of Urology", 153: 1534–1321 (1995).
Tully, J. G., Taylor–Robinson, D., Cole, R.M., Rose, D.L. A Newly discovered mycoplasma in the human urogenital tract, 1981, The Lancet, pp. 1288–1291.
Razin, S. Chapter 37 "Mycoplasmas" in Medical Microbiology, 3rd Edition, pp. 505–516. Ed. by S. Baron Pub. Churchill Livingstone, 1991.
ICA/NIDDK Interstitial Cystitis Scientific Workshop Domingue, G.J., Bost, K. L., Ghoniem, G. M., and Human, L. G. "Cryptic Bacteria in Interstitial Cystis.", Oct. 8, 1993.

Primary Examiner—James C. Housel
Assistant Examiner—Ginny Allen Portner
Attorney, Agent, or Firm—Michael L. Murray

[57] ABSTRACT

The present inventor discloses a description of the preparation of ICAPs for use in diagnosis, methods of prevention and prophylaxis of interstitial cystitis. The forms can be cultivated in high concentrations of serum, they can be visualized in a light microscope, they have a characteristic morphology in an electron microscope, and they are immunogenic and antigenic.

8 Claims, 3 Drawing Sheets

METHODS AND COMPOSITIONS FOR DIAGNOSIS AND TREATMENT OF INTERSTITIAL CYSTITIS

The United States Government may have rights in the present invention as relevant developmental work was supported by a National Institutes of Health Grant DK44812-04.

BACKGROUND OF THE INVENTION

1. Epidemiology

Interstitial cystitis (IC) is a chronic debilitating inflammatory disorder of the bladder. The disease is most common in women ranging in age from about thirty to sixty with onset of the condition typically occurring at about forty years of age.

2. Clinical Presentation

The most prevalent symptoms include severe abdominal pain and urinary urgency two or three times per hour, day and night. Quality of life scores in the most severe patients are lower than in chronic renal disease patients. The initiating causes are unknown and there is no cure known. The condition is categorized as "interstitial cystitis" because it is believed the disease does not affect the surface of the bladder but instead involves the spaces between the cells, namely the interstices, in the lining of the bladder.

It has been suggested that IC may be an autoimmune disease. See Fall et al., J. Urol., 137:35, (1987), for example. Autoimmune diseases have been the subject of widespread attention because of the considerable morbidity worldwide that they cause. Autoimmune diseases include rheumatoid arthritis, type-1 diabetes mellitus (insulin dependent), multiple sclerosis, myasthenia gravis, systemic lupus erythematosus, Sjogren's syndrome, mixed connective tissue disease, experimental allergic encephalomyelitis (EAE), to name a few. In most cases, it is believed that autoimmune diseases result from abnormal cells of the immune system destroying target tissues, either by direct killing or by producing autoantibodies. Current treatment for these diseases remains on an empirical level and is based on causing generalized immunosuppression, either with steroids or other immunosuppressive drugs. This therapeutic approach is also fraught with other problems including associated severe side effects. Further, they serve only to retard the natural progression of these autoimmune diseases. Effective therapeutic treatment, to say nothing of a cure, is beyond present day medical technology. The aberrations in the immune system resulting in these various autoimmune diseases are not well understood, despite the extensive research that has taken place in this field. See Ratliff et al. (1995) Clin. Immunol. Immunopath. 74: 209–216., for example.

3. Diagnosis

Although numerous theories of pathogenesis have been proposed, the etiology of IC is unknown. The hypothesized causes of IC include infectious, lymphovascular obstruction and neurogenic, endocrinologic, psychoneurotic, inflammatory (especially mast cells). and autoimmune pathologies. Some evidence supports the hypothesis that the prevalence of microoganisms, especially bacteria at low concentrations, is greater in the urine of IC patients than of control subjects (Keay, S. et al. (1995) Urology, 45: 223–229 (the contents of which are hereby incorporated by reference). Presently, IC patients are diagnosed clinically by their symptoms, negative urine cultures, absence of other diseases, and cystoscopic findings of glomerulations and/or ulcers. Accordingly, diagnosis is very difficult. It has been found that even a cystoscopic examination, which is the insertion of a long thin viewing instrument into the bladder, will not lead with certainty to a diagnosis. Diagnosis using biochemical and laboratory test also have not proved to be extremely helpful. If no infection or disease is found, a hydrodistentive cystoscopic examination can be carried out under anesthesia. In this procedure the bladder is stretched by filling it with irrigating fluid and the bladder wall is carefully examined cystoscopically. This is the only known way of detecting the characteristic mucosal abnormalities associated with interstitial cystitis, namely the tiny hemorrhages and scar tissue on the bladder wall. Since diagnosis can be uncertain even when using this highly invasive hydrodistention technique, other factors such as case history, urine analysis and culture, bladder biopsy and response to therapy all must also be taken into consideration for a proper diagnosis.

Recently, U.S. Pat. No. 05,318,891 (incorporated herein by reference) disclosed a diagnostic procedure said to be capable of detecting the active inflammatory status of tissue, including that caused by interstitial cystitis and other inflammatory disorders, through the detection of an inflammatory marker in fluid exposed to the inflamed tissue. This procedure will provide positive results only during inflammation and will provide a negative test result when the condition is in remission.

The National Institute of Diabetes, Digestive and Kidney Diseases formed a task force that established a standard diagnosis for IC, published by Gillenwater, J. Y. and Wein, A. J. J. Urol. (1988) 140: 203 (the contents of which are incorporated herein by reference). Table 1 summarizes the standard diagnosis.

TABLE 1

Criteria Required for Inclusion as Interstitial Cystitis

1) One of the following two criteria must be present:
  a. The presence of glomerulations on cystoscopic examination;
    i.) The glomerulations must be diffuse i.e. they must be present in the three quadrants of the bladder and there must be at least ten glomerulations per quadrant; ii.) The examination for glomerulations will occur after distention of the bladder to 80–100 cm water pressure per 1–2 minutes with the patient under anesthesia; iii.) The glomerulations to be considered must not be along the path of the cystoscope; iv.) The bladder may be distended up to two times before evaluation.
  b. The presence of a classic Hunner's ulcer on cystoscopic examination;

1) One of the following two criteria must be present:
  i. Pain associated with the bladder; ii.) Urinary urgency.

The presence of any one of the following criteria will exclude the diagnosis of interstitial cystitis:

Bladder capacity of greater than 350 cc. Specifications: 1.) Demonstration on cystometrogram; 2.) Either gas or liquid CMG; 3.) Patient is awake.

No intense urge to void with bladder filled to 100 cc of gas or 150 cc of water, with a medium rate of fill (30–100 cc/min.).

The demonstration of involuntary bladder contractions on cystometrogram with a medium rate of filling.

The duration of symptoms is less than 9 months.

The absence of nocturia.

The frequency of urination, while awake, is less than 8 times per day.

Symptoms relieved by antimicrobials, antiseptics, anticholinergics or antispasmodics.

Diagnosed bacterial cystitis or prostatitis within 3 months. Must be abacteriuric for 3 months.

Presence of bladder or lower ureteral calculi.

Active genital herpes.

Uterine, cervical, vaginal or urethral CA.

Urethral diverticulum.

Cytophosphomide cystitis.

Vaginitis.

Tuberculous cystitis.

Radiation cystitis.

Benign or malignant tumors.

Age less than 18 years.

TABLE 2

STAINING CHARACTERISTICS

| Routine | Horse Form | Human Form |
|---|---|---|
| Gram | − | − |
| safranin | − | − |
| toludine blue | − | − |
| crystal violet | + | +/− |
| carbol fuchsin | − | − |
| Dienes | − | − |
| lactophenol cotton blue | − | − |
| malachite green | + | + |
| metachromatic granule | − | − |
| methylene blue | − | − |
| India ink | − | − |
| Fluorescent | | |
| acridine orange | + | + |
| DAPI | + | + |
| Chlamydia | − | − |
| Syto-live (11–15) | + | + |
| Live/Dead Bac Light | + | + |

The present inventors used the diagnostic criteria presented in Table 1 to classify prospective subjects as IC cases or controls and in this invention the term "presumptive interstitial cystitis" shall mean a disorder of the bladder that conforms to the standard of Table 1. Subjects not totally conforming to the standard of Table 1, yet demonstrating substantial symptoms compatible with interstitial cystitis are placed in a separate category, termed "painful bladder".

4. Therapy and prevention.

Treatment has been met with very limited success. Dimethyl sulfoxide (DMSO) and clorpactin (Sant, R. R., LaRock, D. R., Urol. Clin. North Am. (1994) 21: 73–83. are sometimes used to alleviate symptoms. Other treatments include bladder distension therapy and sometimes surgical removal of the bladder. The limitations of current therapies result in part from the undetermined cause of the disease.

SUMMARY OF THE INVENTION

The present inventor has made extensive and intensive studies with a view toward solving the above-mentioned problems and developing a diagnostic test and determining methods of prevention and prophylaxis for interstitial cystitis. They have demonstrated the presence of bacterial 16S rRNA genes in bladder biopsies from approximately 40% of patients with IC, but not from control patients with other urological diseases.

It has been found that there exists an interstitial cystitis associated particle (ICAP). This particle can be obtained from a test sample, the test sample being selected from the group consisting of human body fluids, a first serum, a first plasma, and tissue; and filtered through a filter containing pores with a diameter less than or equal to approximately 0.22 μm. The particle has a core, the core having tails of sheets continuing therefrom, and the tails being regularly spaced apart. Moreover, the present inventors have succeeded in cultivating an ICAP from the tissue of 14 of 14 presumptive interstitial cystitis patients and from 1 of 15 controls. These results have been described in the Journal of Urology, (1995) 153: 1321–1326, incorporated herein by reference. They are also presented in detail in the examples. Cultivation of the ICAPs is described in example 3.

Filters of 0.22 μm pore size are the most widely used for sterilization filtration purposes because the pore size is smaller than bacteria. It is used particularly to sterilize serum or plasma where species of pseudomonas, or other small bacteria may be present. Bacteria without cell walls, such as mycoplasma, pass through such filters (Zinsser Microbiology, 20th edition, by Joklik, W. K., H. P. Willett, and D. B. Amos, pub. by Appleton-Century-Crofts, Norwalk Conn. (1992)

It should be recognized that the use of these filters is well known to those skilled in the art of microbiology. Filter manufacturers and suppliers of filters such as Filtron Technology Corp. and Baxter Diagnostics, Inc. provide manuals and catalogs with extensive guidance on the selection of alternative filter compositions, characteristics and usage. Thus, many filters other than the particular examples described herein are enabled.

Cultivation of the ICAP was achieved by the development of a novel medium. Further, the present inventors have found that, formulated in a suitable pharmaceutical vaccine composition, the ICAP elicited a specific immune response in rabbits. Given the subject discovery that the presence of ICAPs is associated with interstitial cystitis, many well-known methods of detecting these analytes can be applied to detect interstitial cystitis and diagnose a disease. Based upon the above-mentioned findings, the present invention has been completed.

It has also been found the ICAP propagates in an enriched cell-free medium, and that the propagation is sensitive to antibiotics except polyene antibiotics and β lactam antibiotics.

These observations are the basis for making a substantially purified ICAP from a naturally occurring state, one method comprising the steps of providing a test sample, the test sample being selected from the group consisting of human body fluids, a first serum, a first plasma, and tissue; and filtering the fluid through a filter containing pores with a diameter less than or equal to approximately 0.22 mm; and collecting the filtrate, wherein the ICAP is retained, the ICAP having a core, the core having tails of sheets continuing therefrom, and the sheets regularly spaced apart.

It has also been found that the ICAP can be stained with certain dyes, whereby a stained ICAP is created.

It has also been found that the ICAP may be separated into component parts. Moreover, components having molecular weights of approximately 28, 58, 68, and 80 kilodaltons react with specific antibodies to form complexes. Further, the components may be distributed into an ordered array, facilitating identification of the ICAP and diagnosis of interstitial cystitis. For example, if a first test sample is provided from a first human, wherein the first human has no symptoms of interstitial cystitis disease, and a second test sample is provided from a second human; and a first diagnostic array is obtained from the first test sample and a second diagnostic array is obtained from the second test sample; and the first and second diagnostic arrays are compared; a report may be prepared stating that a difference in the binding patterns indicates that the second human has a high likelihood of having interstitial cystitis disease.

Further, since propagation of the I CAP is sensitive to antibiotics the present invention includes a method that aids in prescribing treatment for interstitial cystitis in a patient, comprising the steps of:
obtaining a test sample from the patient;
detecting an ICAP by an effective means;
correlating the presence or absence of the ICAP with interstitial cystitis, wherein if
the patient has not previously been diagnosed as having presumptive interstitial cystitis, then the presence of the ICAP indicates that the patient has a need for prophylactic antibiotic therapy;
the patient has not been diagnosed as having presumptive interstitial cystitis, then the absence of the ICAP indicates that the patient has no need for prophylactic antibiotic therapy;
the patient has previously been diagnosed as having an undifferentiated chronic inflammatory disorder of the bladder of autoimmune origin, then the absence of the ICAP indicates that the patient has no need for antibiotic therapy;
the patient has previously been diagnosed as having an undifferentiated chronic inflammatory disorder of the bladder of autoimmune origin, then the presence of the ICAP indicates that the patient has a need for antibiotic therapy;
the patient has previously been diagnosed as having presumptive interstitial cystitis, then the absence of the ICAP indicates that the patient has no need for antibiotic therapy;
the patient has previously been diagnosed as having presumptive interstitial cystitis, then the presence of the ICAP indicates that the patient has a need for antibiotic therapy.

BRIEF DESCRIPTION OF THE DRAWINGS

When core becomes electron dense, sheets are difficult to discern; spacing between individual sheets remains in register of approximately 5 to 7 nm. Periodicity of sheets in tail remains in register as well, and distance between lamellae is same as core. True myelin in nervous system also has periodicity of approximately 5 to 7 nm. However, contrary to true myelin double membrane spacing, spacing of form's membrane-like sheets is tighter. True myelin is mentioned here as a guide for spacing between lamellae. No molecular relationship between myelin structure and these cultured forms is implied. In FIG. 1 note large dense core-like structure with swirls emanating from the dense form. FIG. 2 demonstrates the packing of swirls and myelin-like sheets. FIG. 3 shows a free-standing electron-lucent body with scattered myelin-like sheets that are detached.

DETAILED DESCRIPTION OF THE INVENTION

Definitions

Figure 1:
FIGS. 1–3 show electron micrographs of ICAPs grown from the serum of an interstitial cystitis patient. A serum sample from a control subject tested under the same conditions was negative for these forms. Magnification indicated by calibrated bar.. Forms consist of myelin-like swirl forming core-like structures, and a tail. Core diameter ranges between 40 to 80 nm and can be electron lucent or electron dense. Electron lucent cores display packing of swirls in various configurations, some of which seem geometrically organized. The tail is continution of the core and usually has same number of myelin-like sheets as core. Arrangement of sheets around core is similar to afferent myelinated axons. Electron dense material around forms corresponds to agar used for holding them together during dehydration and embedding.

Before proceeding further with the description of various specific embodiments of the present invention, a number of terms will be defined. A variety of assay techniques in which the object of present invention can be achieved are also described.

Antibodies

Antibodies are a class of globular proteins that are produced by the immune system as a defense against foreign agents. These proteins bind their respective antigen or hapten through a collection of non-covalent interactions (hydrophobic, electrostatic and/or hydrogen bonding interactions). The strength of binding between the antigen and the antibody can vary due to the natural elimination or addition of some of these interactions and the resulting affinity constant (Ka) generally varies between about $10^3$ and about $10^{10}$.

Monoclonal antibodies are a subset of antibodies, and are proteins with a single defined structure and defined amino acid sequence. Monoclonal antibodies are known and desired primarily for their specificity of binding; that is their ability to bind only one compound (antigen or hapten) out of many with very similar structures. However, a recurring problem is the identification and isolation of monoclonal antibodies which have not only great specificity, but also high affinity, i.e. tight binding to its antigen or hapten. Monoclonal antibodies with both high specificity and high affinity are generally identified and isolated only by very laborious screening of many hybridoma cell cultures. Alternatively, genetic techniques may be used to alter specific amino acids in the antibody sequence by site-directed mutagenesis or to generate large numbers of mutations for screening purposes by producing libraries of mutations. These techniques, however, are also very labor intensive.

U.S. Pat. No. 05,367,058 (incorporated herein by reference) provides a solution to the conventional labor intensive methods for isolating monoclonal antibodies with high affinity as it relates to a chemically modified monoclonal antibody or antibody fragment with an increased affinity for its antigen or hapten. The modification to the antibody is a chemical moiety which is capable of covalently bonding to a functional group of the antigen or a chemical functionality which modifies the antigen upon binding of the antigen and antibody. The affinity of the modified monoclonal antibody is at least 10-fold greater than the affinity of a corresponding unmodified antibody for the same antigen or modified antigen. The most preferred modification is the addition of a thiol group on the surface of the antibody such that a covalent bond forms between the antibody and antigen when they bind to one another.

Before proceeding further with the description of various specific embodiments of the present invention, a number of terms will be defined. A variety of assay techniques in which the object of present invention can be achieved are also described.

The term "analyte" refers to either the ICAP antigen or the ICAP antibody.

As used herein, "test sample" or "body fluid sample" typically refer to a naturally occurring or artificially formed liquid test medium suspected of containing the analyte of interest. The test sample is generally a biological fluid or a dilution thereof. Biological fluids from which an analyte can be determined include serum, whole blood, plasma, saliva, amniotic and cerebrospinal fluids, tissue including blood, and other biological fluids and tissues.

The term "indicator reagent" refers to an assay reagent comprising a detectable label directly or indirectly attached to a specific binding member which is capable of directly or indirectly binding to the analyte to indicate the presence, absence or amount of the analyte. A variety of different indicator reagents can be formed by varying either the label or the specific binding member. In general, the indicator reagent is detected after it has formed a complex with either the analyte or a complementary specific binding member, but the unbound indicator reagent can also be detected.

The term "specific binding member" refers to a member of a specific binding pair, i.e., two different molecules wherein one of the molecules through chemical or physical means specifically binds to the second molecule. In addition to antigen and antibody specific binding pairs, other specific binding pairs include biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders, protein A and antibodies, protein G and antibodies, and the like. Furthermore, specific binding pairs can include members that are analogs of the original specific binding member, for example an analyte-analog. If the specific binding member is an immunoreactant it can be, for example, an antibody, antigen, hapten, or complex thereof. If an antibody is used, it can be a monoclonal or polyclonal antibody, a recombinant protein or antibody, a mixture(s) or fragment(s) thereof, as well as a mixture of an antibody and other specific binding members. The details of the preparation of such antibodies and their suitability for use as specific binding members are well-known to those skilled-in-the-art.

The term "label" refers to any substance which is attached to a specific binding member and which is capable of producing a signal that is detectable by visual or instrumental means. Various suitable labels for use in the present invention can include chromogens, catalysts, fluorescent compounds, chemiluminescent compounds, radioactive labels, direct visual labels including colloidal metallic and non-metallic particles, dye particles, enzymes or substrates, or organic polymer latex particles, liposomes or other vesicles containing signal producing substances, and the like.

The term "signal producing component" refers to any substance capable of reacting with another assay reagent or the analyte to produce a reaction product or signal that indicates the presence of the analyte and that is detectable by visual or instrumental means. "Signal production system", as used herein, refers to the group of assay reagents that are needed to produce the desired reaction product or signal. For example, one or more signal producing components can be used to react with a label and generate the detectable signal, i.e., when the label is an enzyme, amplification of the detectable signal is obtained by reacting the enzyme with one or more substrates or additional enzymes to produce a detectable reaction product.

The term "capture binding member" refers to a specific binding member which can directly or indirectly bind the analyte or indicator reagent and which is bound or is capable of being bound to a solid phase, or is capable of being precipitated, such that the capture binding member can be separated from the test sample and other assay reagents by any means. The term "capture reagent" refers to a capture binding member which is directly or indirectly attached to a solid phase material to enable the separation of the capture binding member, and analyte or indicator reagent that is bound thereto, from unbound analyte and assay reagents. Typically, the attachment of the capture binding member to the solid phase material is substantially irreversible and can include covalent mechanisms. The capture reagent of the present invention, however, is not limited to a capture binding member bound to an insoluble solid phase material. In an agglutination assay, the capture binding member of the capture reagent can be bound to a soluble carrier material such as bovine serum albumin.

The term "solid phase material" refers to any suitable chromatographic, bibulous, porous or capillary material or other conventional solid material, well-known to those skilled-in-the-art, used to immobilize specific binding members. In the present invention, the solid phase material can include a fiberglass, cellulose or nylon pad for use in a flow-through assay device having one or more layers containing one or more of the assay reagents; a dipstick for a dip and read assay; a test strip for chromatographic (e.g., paper or glass fiber) or thin layer chromatographic (e.g., nitrocellulose) techniques in which one or all of the reagents are contained in separate zones of a single strip of solid phase material; or an absorbent material well-known to those skilled-in-the-art. The solid phase material can also include, without limitation, polyacrylamide beads, polystyrene beads or tubes, magnetic beads, a microtitre plate or a glass or plastic test tube.

Natural, synthetic or naturally occurring materials that are synthetically modified including polysaccharides, e.g., cellulose materials such as paper and cellulose derivatives such as diazobenzyloxymethylcellulose, nitrocellulose, 2-aminophenylthioetheylcellulose, and cellulose acetate; silica; silicon particles; inorganic materials such as deactivated alumina, or other inorganic finely divided material uniformly dispersed in a porous polymer matrix, with polymers such as vinyl chloride, vinyl chloride polymer with propylene, and vinyl chloride polymer with vinyl acetate; cloth, both naturally occurring (e.g., cotton) and synthetic (e.g., nylon); porous gels such as silica gel, agarose, dextran, and gelatin; polymeric films such as polyacrylates; protein binding membranes; and the like, can be used as a solid phase material. The solid phase material should have reasonable strength or strength can be provided by means of a support, and the solid phase material should not interfere with the production of a detectable signal.

"Blocking" is a term that describes procedures used to prevent nonspecific adsorption of immunological reagents to a solid phase material. Blocking methods are well known to those skilled in the art.

Optionally, the specific binding member of the capture reagent can be affixed to particles, e.g., microparticles. These microparticles can serve as the solid phase material and be retained in a column, suspended in a mixture of soluble reagents and test sample, or retained and immobilized by another solid phase base material. By "retained and immobilized" is meant that the microparticles, associated with the solid phase base material, are not capable of substantial movement to positions elsewhere within that material. The microparticles can be selected by one skilled-in-the-art from any suitable type of particulate material including those composed of polystyrene, polymethylacrylate, polypropylene, polytetrafluoroethylene, polyacrylonitrile, polycarbonate or similar materials. The size of the microparticles is not critical, although it is preferred that the average diameter be smaller than the average pore size of the solid phase base material if such is used.

The homogeneous assay configurations do not require the separation of the test solution and the indicator reagent prior to the detection of the indicator reagent or binding complexes. This broad classification includes many formats such as agglutination and precipitation assays as well as others known to those skilled-in-the-art for the detection of analytes. Both direct and indirect agglutination assays can be performed.

The term "ancillary specific binding member" refers to a specific binding member used in addition to the capture binding member and the indicator reagent which becomes a part of the detectable binding complex. One or more ancillary specific binding members can be used in an assay. For example, an ancillary specific binding member can be used in an assay where the indicator reagent is capable of binding the ancillary specific binding member which is in turn capable of binding the analyte.

The homogeneous assay configurations do not require the separation of the test solution and the indicator reagent prior to the detection of the indicator reagent or binding complexes. This broad classification includes many formats such as agglutination and precipitation assays as well as others known to those skilled-in-the-art for the detection of analytes. Both direct and indirect agglutination assays can be performed.

The object of the present invention can be achieved by a variety of binding assay configurations and formats which enable the detection or measurement of ICAP antigen and/or ICAP antibody to diagnose, stage or predict the course of IC. The ICAP antigen and ICAP antibody would be readily detectable in urine, serum and biopsy test samples by means of binding assays which are generally categorized into one of two major classes, homogeneous and heterogeneous assays. These assays may be further divided into sandwich and competitive assay formats, and variations thereof.

In a solid phase sandwich assay, the capture reagent typically involves a specific binding member which has been bound to a solid phase material. For example, the specific binding member can be an immobilized antibody which will bind to an antigen-analyte in the test sample, or the specific binding member can be an immobilized antigen which will bind to an antibody-analyte in the test sample. The capture reagent is contacted to a test sample, suspected of containing the analyte, and to an indicator reagent comprising a second specific binding member that has been labeled, for example, a labeled anti-analyte antibody. The reagents can be mixed simultaneously or added sequentially, either singly or in combination. A binding reaction results in the formation of a capture reagent/analyte/indicator reagent complex immobilized upon the solid phase material. The assay can also comprise the step of separating the resultant complex from the excess reagents and test sample. The complex retained on the solid phase material is detected by examining the solid phase for the indicator reagent. If analyte is present in the test sample, then label will be present on the solid phase material. The amount of label on the solid phase is a function of the amount of analyte in the test sample.

The homogeneous assay configurations do not require the separation of the test solution and the indicator reagent prior to the detection of the indicator reagent or binding complexes. This broad classification includes many formats such as agglutination and precipitation assays as well as others known to those skilled-in-the-art for the detection of analytes. Both direct and indirect agglutination assays can be performed.

It will be appreciated by those skilled-in-the-art that the selection of any given label, binding member, ancillary binding member or solid phase material is generally not critical to the present invention. The materials are chosen to optimize the results provided by the chosen assay configuration.

The present inventors have made extensive and intensive studies with a view toward solving the above-mentioned problems and developing a diagnostic test for interstitial cystitis. They have demonstrated the presence of bacterial 16S rRNA genes in bladder biopsies from approximately 40% of patients with IC, but not from control patients with other urological diseases. Moreover, the present inventors have succeeded in cultivating a "ICAP" from the tissue of 14 of 14 presumptive interstitial cystitis patients and from 1 of 15 controls. The ICAP passes through membrane filters containing pores of 0.22 µm and 0.1 µm diameter. These results have been described in the Journal of Urology, (1995) 153: 1321–1326, incorporated herein by reference. They are also presented in detail in example 2. Cultivation of the ICAPs is described in example 3. Filters of 0.22 µm pore size are the most widely used for sterilization filtration purposes because the pore size is smaller than bacteria. It is used particularly to sterilize serum or plasma where species of pseudomonas, or other small bacteria may be present. Bacteria without cell walls, such as mycoplasma, pass through such filters (Zinsser Microbiology, 20th edition, by Joklik, W. K., H. P. Willett, and D. B. Amos, pub. by Appleton-Century-Crofts, Norwalk Conn. (1992) Cultivation of the ICAP was achieved by the development of a novel medium. Further, the present inventors have found that, formulated in a suitable pharmaceutical vaccine composition, the ICAP elicited a specific immune response in rabbits. Based on the above-mentioned findings, the present invention has been completed.

Amphotericin B, erythromycin, nalidixic acid and penicillin were tested to determine whether any growth inhibitory action could be demonstrated against the ICAPs. The mode of action of these antibiotics is described by (Zinsser Microbiology, 20th edition, by Joklik, W. K., H. P. Willett, and D. B. Amos, pub. by Appleton-Century-Crofts, Norwalk Conn. (1992) (incorporated herein by reference). Penicillin is a β-lactam antibiotic, characterized by the presence of a four-member β-lactam ring. Included in the group are the penems, carbapenems, oxaphems, clavams, and monobactams. The target of β-lactam antibiotics is the growing cell wall. Mycoplasma are unique among the eubacteria in not having this target of β-lactam antibiotic action, and thus are resistant to β-lactam antibiotics. Erythromycin and nalidixic acid were completely inhibitory at all concentrations. Amphotericin B was not inhibitory, suggesting that these forms are not fungi. Amphotericin B is a polyene antibiotic. The polyenes selectively inhibit organisms whose membrane contain sterols. They are active against yeast, fungi, and other eucaryotic cells but are not inhibitory for procaryotic organisms. All polyene antibiotics have a large lactone ring; amphotericin B and nystatin are the most important polyene antibiotics. Penicillin was also not inhibitory, suggesting that the forms do not have a cell wall, since the mode of action of penicillin is to inhibit cell wall synthesis of bacteria). The inhibition of growth by erythromycin and naladixic acid suggest that these forms may be bacterial in origin.

ICAPs can also be cultivated from pooled human sera obtained from BioWhittaker, Inc. Since these sera represent a pool of the serum from many individuals of unknown health status, the presence of ICAPs within the pool cannot be correlated with any medical condition. It may be significant, however, that screening tests using ICAP antibody could be developed to detect and eliminate any potential hazard that these forms represent when present in serum products.

Inventive Methods of Diagnosis

The present invention provides a method of diagnosing interstitial cystitis in a subject comprising cultivating and detecting the presence of an analyte in a human subject. The analyte comprises "ICAPs" or an immunogenically specific determinant thereof (hereinafter collectively referred to as "ICAP antigen") and antibodies from the subject that are specifically reactive with ICAP antigen As used herein, an "immunogenically specific determinant" can be on an intact ICAP or a fragment thereof.

Given the subject discovery that the presence of ICAPs is associated with interstitial cystitis, many well-known methods of detecting these analytes can be applied to detect interstitial cystitis and diagnose a disease.

The ICAPs contain DNA as detected by nucleic acid specific stains and by the phenol-chloroform method for chemical extraction of DNA. The structures do not appear to be osmotically fragile, as they can grown in nonsomotically stabilized media (approximately 300 mOsm./kg $H_2O$. They do not gram stain, but are stained by malachite green. They have an absolute requirement for serum for growth. The ICAP's unusual ultrastructure suggests that the ICAPs represent a novel class of organism that has been discovered by the present inventors. Further details are provided in the examples.

In one example of the method of diagnosing interstitial cystitis, tissue test samples obtained from a patient exhibiting systems suggestive of IC, are innoculated into media suitable for the cultivation of ICAPs. After incubation, the presence of ICAPs is detected by staining and microscopic examination. The present inventors have demonstrated that malachite green, crystal violet, acridine orange, "Syto-live™", and "live/dead BacLight™" are effective stains for ICAPs. Other staining techniques, however, are well known to those skilled in the art, and some of these also could be suitable for detecting ICAPs.

The forms are stained with nucleic acid stains, suggesting the presence of nucleic acids. For example, the fluorescent dye (fluorochrome), acridine orange (AO), is a small, fluorescent, planar cationic vital dye which, in the unfixed cell, complexes with intranuclear nucleic acids as well as other intracellular polyanionic biopolymers. Because of its special affinity for the nucleic acids, AO has the property of differentiating ribonucleic acid (RNA) from deoxyribonucleic acid (DNA). In a solution of optimum acidity, the AO-RNA combination fluoresces an orange-pink color and the AO-DNA combination fluoresces a yellowish-green color. The intensity of fluorescence in each combination depends on the concentrations of respective nucleic acids. When a high concentration of RNA is present such as is the case with fast growing cells, the cytoplasm and the nucleoli may show a fluorescence of a brighter orange-red. ICAPs disclosed by the present inventors stain both orange and green; detailed results are shown in example 4.

"Syto-live™" and "BacLight™" staining also suggest the presence of nucleic acid. This stain is disclosed in U.S. Pat. No. 05,314,805 (incorporated herein by reference). The "BacLight™" stain provides a method for simultaneously or sequentially assessing the viability of cells by using a unique combination of fluorogenic reagents, calcein AM and ethidium homodimer. Following the use of this invention, the cells of a given sample or population are stained either red or green. "Live" cells, i.e. cells with an intact membrane in which esterase activity is occurring, are distinguished by an intense uniform green fluorescence generated by the enzymatic hydrolysis of calcein AM. The "Syto-live™" stain also produces an intense green fluorescence when live cells are stained. The Calcein AM is membrane permeable and virtually non-fluorescent. Once inside the cell, calcein AM is hydrolysed by intracellular esterase activity to yield an intensely fluorescent product, calcein. Calcein is a polyanionic molecule that is well retained within live cells.

Dead cells or cells whose membrane integrity has been damaged are distinguished by a bright red fluorescence resulting from ethidium homodimer binding to nucleic acids when "BacLight™" staining is used. Ethidium homodimer is excluded from live cells, but the loss of cell membrane integrity allows the dye to enter the cell. The fluorescence of ethidium homodimer undergoes a 40-fold enhancement upon binding to nucleic acids. Calcein AM and ethidium homodimer are both available commercially from Molecular Probes, Inc., Eugene Oreg. ICAPs disclosed by the present inventors stain green using "Syto-live™" or "BacLight™" staining; detailed results are presented in example 4.

The use of 4',6-diamidino-2-phenylindole (DAPI) and of acridine orange stains to enumerate bacteria is reviewed by Kepner, R. L., Jr. and Pratt, J. R. (1994) Microbiol. Rev. 58: 603–615 (incorporated herein by reference). DAPI is described by Jeppesen, C. and Nielsen, P. E. (1989) Eur. J. Biochem., 182: 437 (incorporated herein by reference).

In one example of the method of diagnosing interstitial cystitis, the step of detecting ICAPs antigen is performed by contacting a fluid or tissue sample from the subject with an amount of a purified ligand, e.g. antibodies, specifically reactive with ICAPs antigen and detecting the reaction of the ligand with ICAP antigen. As contemplated herein, the ligand can be an antibody, a fragment of an antibody or another reagent that has reactivity with the antigen. The test sample of this method can comprise any body tissue which would contain ICAPs or from which ICAPs can be cultivated. The present inventors have cultivated ICAPs from urine, serum and biopsy tissue.

In an alternative embodiment, the method of diagnosing IC of the present invention can be such that the presence of ICAP is determined by detecting the presence of an antibody from the subject which is specifically reactive with ICAP antigen. The presence of antibody specifically reactive with ICAP indicates the presence of infection by ICAP. As used herein, the term "specifically reactive" denotes an antibody or other ligand that does not cross react substantially with any antigen other than the one specified, in this case, ICAP antigen.

When the method of diagnosing IC is by detecting the presence of an antibody specifically reactive with ICAP antigen, the step of detecting the presence of an antibody specifically reactive to ICAP antigen can, for example, include the steps of contacting a fluid or tissue test sample from the subject with an amount of ICAP antigen to react with an antibody specifically reactive with ICAP antigen and detecting the reaction of the ICAP antigen with the antibody. Methods of conducting such a diagnosis are illustrated in examples 8 and 9.

Detecting the reaction of the ligand with ICAP antigen can be facilitated by the use of a ligand that is bound to a label. Such a label will allow visual detection of a precipitate or an indicator change, visual detection by microscopy, or automated detection by spectrometry or radiometric measurement or the like. Examples of detectable moieties include fluorescein and rhodamine (for fluorescence microscopy), horseradish peroxidase (for either light microscopy or electron microscopy and biochemical detection), biotin-strepavidin (for light or electron microscopy) and alkaline phosphatase (for biochemical detection by indicator change). The detection method and label used can be selected from the list above or other suitable examples by the standard criteria applied to such selections (Harlow and Lane, Antibodies: A Laboratory Manual, Cold Spring Harbor Laboratory, Cold Spring Harbor, N.Y., 1988).

In the diagnostic methods of the present invention, the step of detecting the reaction of the specific binding member with ICAP antigen can be further aided, in appropriate instances, by the use of a ancillary antibody or other ancillary specific binding member which is reactive, either specifically with a different epitope or nonspecifically with the specific binding member or reacted antibody.

In the diagnostic method which detects the presence of an antibody specifically reactive with ICAP antigen, the ICAP antigen can be bound to a solid phase material and contacted by a body fluid is ample such as blood, plasma or serum. This sample can be taken directly from the patient or in a partially purified form. In this manner, antibodies specific for ICAP antigen (the primary antibody) will specifically react with the bound ICAP antigen. Thereafter, a labelled ancillary antibody or other ancillary specific binding member can be added to enhance the detection of the primary antibody. Generally, the ancillary binding member will be selected for its ability to react with multiple sites on the primary antibody. Thus, for example, several molecules of the ancillary binding member can react with each primary antibody, making the primary antibody more detectable.

Detecting methods such as immunofluorescence assays (IFA) and enzyme linked immunosorbent assays (ELISA) can be readily adapted to accomplish the detection of both ICAP antigen and antibodies specifically reactive therewith. An example of an IFA protocol is provided in Example 8. The indirect immunocytochemical methods taught in Example 8 will be generally applicable for the detection of antigens or antibodies.

An ELISA method effective for the diagnosis of IC based on the detection of human IgG antibodies can, for example, be as follows: (1) bind the antigen (ICAP antigen) to a solid phase material; (2) contact the bound antigen with a serum test sample, containing antibodies reactive with ICAP antigen, from a subject; contact the above with a signal production system exemplified by the following steps: (3) contact a labelled (e.g., horseradish peroxidase enzyme or alkaline phosphatase enzyme) ancillary specific binding member such as anti-human IgG antibody (ancillary antibody); (4) contact the above with the substrate for the enzyme; (5) contact the above with an indicator reagent; (6) observe indicator change in the presence of IgG antibody specifically reactive with ICAP antigen.

A modification of the above ELISA effective for diagnosis of IC based on the detection of human IgM antibodies can be as follows: (1) bind a capture binding member such as an anti-human IgM antibody capable of reacting with a human IgM antibody to a solid phase material (antibody capture); (2) contact the bound antibody with a serum test sample from a subject; (3) contact the above with ICAP antigen; (4) contact the above with a rabbit anti-ICAP antibody; (5) contact the above with an anti-rabbit antibody bound to a label (e.g., horseradish peroxidase enzyme); (6) contact the above with substrate for the enzyme; (7) contact the above with an indicator reagent; (8) observe an indicator change in the presence of an IgM antibody specifically reactive with ICAP antigen.

Another immunologic technique that can be useful in the detection of ICAP infection utilizes monoclonal antibodies for detection of antibodies specifically reactive with ICAP antigen. In a prospective example, sera from the subject is reacted with ICAP antigen bound to a solid phase material (e.g. an ELISA 96-well plate). Excess sera is thoroughly washed away. A labeled (enzyme-linked, fluorescent, radioactive, etc.) monoclonal antibody is then reacted with the previously reacted antigen-serum antibody complex. The amount of inhibition of monoclonal antibody binding is measured relative to a control (no patient serum antibody). The degree of monoclonal antibody inhibition is a very specific test for a particular species since it is based on monoclonal antibody binding specificity.

A micro-agglutination test can also be used to detect the presence of ICAP in a subject. In a prospective example, a solid phase material such as latex beads (or red blood cells) are coated with ICAP antigen and mixed with serum from the subject, such that antibodies in the tissue or body fluids that are specifically reactive with ICAP antigen crosslink with the antigen, causing agglutination. The agglutinated antigen-antibody complexes form a precipitate, visible with the naked eye. In a modification of the above test, antibodies specifically reactive with ICAP antigen can be bound to the beads and antigen in the serum thereby detected. Other fluids of a subject can be effectively used.

In addition, as in a typical sandwich assay, the antibody is bound to a solid phase material and reacted with an ICAP antigen. Thereafter, a ancillary labeled antibody is bound to epitopes not recognized by the first antibody and the ancillary antibody is detected. The sandwich immunoassay can be used in a variety of formats using either monoclonal antibodies on both sides, a monoclonal on one side and a polyclonal on the other side, or polyclonals on both sides. Further, the sandwich assay can be forward, reverse, or simultaneous sandwich assay as described in U.S. Pat. No. 4,376,110 issued Mar. 8, 1983, the contents of which are hereby incorporated by reference.

Western Blot Assay

Western blotting is a rapid sensitive assay for detecting and characterizing proteins by utilizing the specificity an antibody has for a particular antigen. The technique can use both monoclonal and polyclonal antibodies.

The Western Blotting Assay used within the present invention is the conventional assay as described by Ausubel et al., Current Protocols in Molecular Biology, Greene Publishing Associates and Wiley-Interscience (1987). The cell proteins of ICAPs are solubilized, usually with sodium dodecyl sulfate (SDS), urea, and/or other reducing agents such as 2-mercaptoethanol. Subsequently, the solubilized ICAP proteins are separated by sodium dodecyl sulfate polyacrylamide gel electrophoresis (SDS-PAGE) or other separatory techniques, (e.g., thin layer chromatography). The proteins are then electrophoretically transferred or blotted onto nitrocellulose paper, or other conventional suitable materials, (e.g., nylon filters), where the proteins are bound irreversibly (hereinafter an immunoblot). The paper is generally blocked to prevent non-specific binding of ICAP antibody and is then probed with the anti-ICAP. A labelled-anti-immunoglobulin (Ig) conjugate directed towards the anti-ICAP is added to the paper and incubated under conditions which allow the binding of the two antibodies to occur. The label on the second antibody can be conventional labels such as an enzyme (e.g., peroxidase), radioisotope or flourescent molecule.

In one format, an immunoabsorbent is formed by attaching an anti-ICAP antibody to a solid phase. Biological fluid is contacted with the immunoabsorbent under conditions (e.g., incubation) which allow binding of the antibodies to the ICAP protein to occur. Subsequently, a second labelled monoclonal antibody reactive with ICAP is added to the mixture under conditions (e.g., incubation) which allow binding to occur between the second antibody and ICAP antigen. The label of the bound antibody is measured as an indication of the presence or absence or the quantity of ICAP in the test sample.

Another format for a sandwich assay uses both a monoclonal antibody and polyclonal antibodies. The monoclonal antibody can be used as either capture antibody or the detector antibody. When used as the capture antibody, an immunoabsorbent is formed by attaching the monoclonal antibody to a solid phase. The biological fluid to be tested is contacted with the immunoabsorbent under conditions (e.g., incubation) which allow binding of the antibody to the antigen to occur. Subsequently, labelled polyclonal antibodies are added to the biological fluid under conditions (i.e., incubation) which allow binding to occur. The label of the bound or the free antibody can be measured as an indication of the presence or absence of ICAP in the test sample. The above sandwich assays can be modified such that they become indirect sandwich assay wherein the detector polyclonal antibodies or monoclonal antibody is not labelled and a labelled antibody directed toward the detector polyclonal antibodies or monoclonal antibody are added to the reaction mixture under conditions (e.g., incubation) which allow binding of the labelled antibody to the anti-ICAP antibody to occur.

The above-described immunoassays can be used to quantitate the ICAP in a test sample by establishing a standard curve. A standard curve relating quantity of ICAP to a value indicative of the amount of the particular of the label, (e.g., absorbance) can be established using standards having known ICAP content. After preparation of such a curve, the quantity of ICAP in a test sample can be determined by extrapolating a quantity of ICAP from the curve upon obtaining a value indicative of the amount of label (e.g., absorbance). The assays described above would provide physicians with a quick and reliable method of determining whether an individual is afflicted with IC.

The specific reagents and protocols for use in the detection methods described above and similar indirect immunocytochemical methods can be selected from those available in the art based on standard criteria (Harlow and Lane, Antibodies: A Laboratory Manual, Cold Spring Harbor Laboratory, Cold Spring Harbor, N.Y., 1988).

Inventive composition: Diagnostic kit and components thereof.

The present invention further provides a kit for the diagnosis of IC. Such a kit can be an ELISA kit and can comprise the substrate, antigen, primary and ancillary antibodies when appropriate, and any other necessary reagents such as a a signal production system comprizing, for example, detectable moieties, enzyme substrates and indicator reagents as described above. The diagnostic kit can, alternatively, be an IFA kit generally comprising the components and reagents described in Example 8 below. It is contemplated that the diagnostic kits will further comprise a positive and negative control test.

The particular reagents and other components included in the diagnostic kits of the present invention can be selected from those available in the art in accord with the specific diagnostic method practiced in the kit. Such kits can be used to detect ICAP antigen and antibodies specifically reactive therewith in tissue and fluid test samples from a subject and in cultures of ICAPs obtained from the tissue or fluids of a subject.

A nonpathogenic ICAP antigen can be derived by modifying the ICAP organism using standard techniques. For example, the whole cell antigen can be subjected to gamma irradiation to render the ICAP nonpathogenic. Other standard methods of inactivating whole cell antigen include treatment with β-propriolactone or formalin (Harlow and Lane, Antibodies: A Laboratory Manual, Cold Spring Harbor Laboratory, Cold Spring Harbor, N.Y., 1988).

Alternatively, an immunogenically specific determinant of ICAP can be isolated from the whole organism by chemical or mechanical disruption of the organism. For example, a carbohydrate moiety of ICAP can be obtained by standard methods such as digesting ICAP with a protease to remove protein moieties. The carbohydrate moieties thus obtained can be tested to determine their immunogenicity and specificity by the usual methods. Briefly, various concentrations of a putative inactivated (nonpathogenic) immunogenically specific determinant are prepared and administered to an animal and the immunological response (i.e., the production of antibodies) of an animal to each concentration is determined. The amounts of antigen or inactivated or modified-live organism administered depend on the subject, e.g. a human or a cat, the condition of the subject, the size of the subject, etc. Thereafter an animal so inoculated to the nonpathogenic antigen can be exposed to the pathogenic organism to test the potential vaccine effect of the immunogenically specific determinant. (Harlow and Lane, Antibodies: A Laboratory Manual, Cold Spring Harbor Laboratory, Cold Spring Harbor, N.Y., 1988).

Alternatively, a protein moiety of ICAP can be obtained by treating the whole organism with an ionic detergent such as sodium dodecyl sulfate or a nonionic detergent such as Triton X-100 ($C_{.34}$ $H_6$ $O_{11}$ average) or ethylphenyl-polyethylene glycol ("NP-40"™, Shell Oil Company). The protein fragments so obtained can be tested for immunogenicity and specificity as described above. Other immunogenically specific determinants of ICAP can be obtained by the standard methods described above.

The nonpathogenic ICAP antigen of this invention can be used in the construction of a vaccine comprising an immunogenic amount of ICAP antigen and a pharmaceutically acceptable carrier. This ICAP antigen can be killed, modified live or immunogenic fragments of ICAP. Alternatively, mixtures of intact ICAP and immunogenic fragments can be used. The vaccine can then be used in a method of preventing IC in a subject by administering the vaccine to the subject.

The pharmaceutically acceptable carrier in the vaccine of the instant invention can comprise saline or other suitable carriers (Arnon, R. (Ed.) Synthetic Vaccines I:83–92, CRC Press, Inc., Boca Raton, Fla., 1987). An adjuvant can also be a part of the carrier of the vaccine, in which case it can be selected by standard criteria based on the particular ICAP antigen used, the mode of administration and the subject (Arnon, R. (Ed.) Synthetic Vaccines I:93–103, CRC Press, Inc., Boca Raton, Fla., 1987). Methods of administration can be by oral or sublingual means, or by injection, depending on the particular vaccine used and the subject to whom it is administered.

It can be appreciated from the above that the vaccine can be used as a prophylactic or a therapeutic. Thus, subjects with the disease can be treated utilizing the vaccine.

Immunogenic amounts of ICAP antigen can be determined using standard procedures. Briefly, various concentrations of a putative inactivated (nonpathogenic) immunogenically specific determinant are prepared, administered to an animal and the immunological response (i.e., the production of antibodies) of an animal to each concentration is determined.

Thus, the invention provides methods of preventing or treating an ICAP infection and the associated disease by administering the vaccine to a subject.

Other inventive compositions

Other compositions of this invention include a purified ICAP bound to a specific binding member, e.g. an antibody. The term "purified" is used herein to describe antigens, antibodies and other specific binding members that are substantially free of other components of serum, blood or other body fluids, or other proteins associated with ICAP in vivo.

A purified ICAP antigen bound to a solid phase material and a specific binding member specifically reactive with ICAP antigen are also contemplated. Such a purified specific binding member specifically reactive with ICAP antigen can be an antibody. The antibody can be a monoclonal antibody obtained by standard methods. The monoclonal antibody can be secreted by a hybridoma cell line specifically produced for that purpose (Harlow and Lane, Antibodies: A Laboratory Manual, Cold Spring Harbor Laboratory, Cold Spring Harbor, N.Y., 1988). Likewise, polyclonal antibodies specifically reactive with ICAP antigen are within the scope of the present invention. The polyclonal antibody can also be obtained by the standard immunization and purification protocols (Harlow and Lane, Antibodies; A Laboratory Manual, Cold Spring Harbor Laboratory, Cold Spring Harbor, N.Y., 1988). In addition, antibodies modified to enhance their affinity for ICAP antigen are within the scope of the present invention (U.S. Pat. No. 05,367,058).

The antibody can be bound to a solid phase material or labeled or both bound and labeled. The labels contemplated with the composition of the present invention are those listed above in the description of the diagnostic methods, including fluorescent, enzymatic and radioactive markers.

The compositions of the instant application further include an ancillary specific binding member reactive to a unique portion of an antibody specifically reactive with ICAP antigen (primary antibody). The ancillary specific binding member can further comprise a label. As described above, the reaction of the ancillary specific binding member with the primary antibody specifically reactive with ICAP antigen facilitates detection of the reaction of primary antibody with ICAP antigen.

An isolated immunogenically specific determinant or fragment of ICAP is also provided. The manner of obtaining such determinants is as described above for the construction of vaccines.

The following examples are intended to illustrate but not limit the invention. While they are typical of those that might be used, other procedures known to those skilled in the art may be alternatively employed.

EXAMPLE 1

Diagnostic Criteria

The diagnostic criteria of inclusion as interstitial cystitis followed that established by the National Institute of Diabetes, Digestive and Kidney Diseases as shown in Table 1 and in Gillenwater and Wein, perviously cited.

EXAMPLE 2

Preparation of ICAPs

For all IC and all control subjects, venipuncture was performed and approximately 5–10 ml of blood was collected into a sterile vacutainer tube containing no additives. The blood was allowed to clot. The tubes were centrifuged at 2500 rpm for about 10 minutes. The serum was collected and about 1 to 1.5 ml aliquots were placed into sterile screw cap microtubes (Sarstedt). Some serum was stored at −70° for future use. An aliquot (1 to 1.5 ml) of fresh serum was forced under pressure from a syringe through a cellulose acetate membrane containing 0.22 μm diameter pores. The filters were manufactured by "Nalgene™" and were contained in a modified acrylic housing.

In other similar experiments, frozen aliquots were thawed and then filtered.

In other similar experiments, filters containing 0.1 μm diameter pores were used. These filters were manufactured by "Anotec™".

In other similar experiments, filters manufactured by "Anotec™" with a pore diameter of approximately 0.02 μm were used. In these experiments, the serum would not pass through the filter.

Preparation of ICAPs from Urine Specimens

A catheterized urine specimen was obtained from an interstitial cystitis patient, sedimented by centrifugation and drops of the sediment were placed on the surface of the PPLO agar plates and in PPLO broth. Both agar and broth cultures contained 25% horse or human serum (heated at 60° C. for two hours and unheated).

A biopsy of the urinary bladder (cold-cup biopsy), approximately 1–5 mg in weight was placed in a glass tissue grinder with 1 ml PPLO broth for disruption of the tissue and cells. Drops of the ground tissue were placed on the surface of PPLO agar plates and in PPLO broth containing serum as above. In several instances, the patient's own serum was used as the source of 25% serum in the medium. The plates and tubes were incubated at 35° C., under 5% CO2 and anaerobically. Specimens obtained from control subjects were processed as above for patients.

After approximately 10–15 days, filamentous colonies appear in agar rsembling mycoplasma-like organisms. In broth culture, acridine orange fluorescent stained round forms were visible after approximately 10 days incubation. To date, 46 interstitial cystitis patients and 46 control subjects (serum, urine and biopsy urinary bladder tissue)

have been cultured. Definitive conclusions on growth of the ICAPs have been drawn on 14 interstitial cystitis patients and 15 control subjects. ICAPs were isolated from the biopsy bladder tissue of 14/14 interstitial cystitis patients and 1/15 control subjects; from 14/14 urine specimens of interstitial cystitis patients and 3/15 control subjects; and from 14/14 serum specimens of interstitial cystitis patients and 1/10 control subjects. Of 18 supposedly normal subjects outside the interstitial cystitis study, 2/18 had fluorescent round forms in the serum cultures. These two individuals had recently had bacterial infections unrelated to interstitial cystitis.

EXAMPLE 3

Cultivation of ICAPs

Serum Requirement

Aliquots of serum that had been filtered through 0.22 μm diameter pores were cultured in several concentrations of serum, 1.0%, 10%, 50%, and 100% serum, and a control with no serum. For cultivation in 100% serum, an aliquot of filtrate was simply incubated at 35° C. For lower concentrations, the serum was diluted into PPLO medium. The PPLO medium was manufactured by Difco. It contains bacto beef heart infusion (50 g), bacto peptone (10 g), sodium chloride (5 g). PPLO medium (35 g) was dissolved in 1000 ml of distilled water, autoclaved at 121° C., 15 lbs. pressure, for 15 minutes. The autoclaved medium was supplemented with 15% yeast extract purchased from Gibco. The yeast extract was purchased in solution. The yeast extract solution was filtered through a filter containing 0.22 um pores prior to adding to the autoclaved PPLO medium at a final concentration of 15% yeast extract.

The 1.0% serum cultures did not produce ICAPs after approximately 4 months of incubation. The higher serum concentration cultures all yielded ICAPs after approximately 2–3 weeks of incubation. The yield of ICAPs increased with serum concentration and with time. Between the 50% serum and 100% serum cultures, there was approximately a 2 log difference in the number of acridine orange staining round bodies after approximately 4 months of cultivation. About $10^6$ acridine orange stained bodies were seen after about 4 months culture in 100% serum. A similar number of bodies were seen without stain, utilizing phase microscopy. Cultures containing 50% serum yielded only approximately $10^4$ acridine orange staining bodies over the same time period. At 10% serum, the number of ICAPs was reduced about 90%. At less than 10% serum, no ICAPs were observed. Cultures containing just PPLO culture medium without serum yielded no acridine orange staining bodies.

A number of other culture variables were investigated:

Cholesterol was substituted for serum in growth experiments similar to those described above. It was found that cholesterol would not support growth of the ICAPs.

Temperature

Freezing has no effect on development of forms: they do not grow at 4° C. Tubes subjected to 60° C. for 2 hours produce only about 1% ICAPs. Frozen serum retained ability to produce ICAPs upon incubation. Incubation at 4° C. did not produce ICAPs from any inoculum. Heating to 60° C. for 2 hours reduced the production of ICAPs, after incubation in the presence of serum, by over 90%.

Oxygen had no effect on the growth of ICAPs; incubation under anaerobic conditions produced the same level of ICAPs as incubation in the presence of atmospheric oxygen.

Increased $CO_2$ (5%) had no effect on ICAP production.

Growth Inhibition by Antibiotics

Amphotericin B, erythromycin, nalidixic acid and penicillin were tested to determine whether any growth inhibitory action could be demonstrated against these forms. The antibiotics in solution were diluted in serial 2 fold dilutions ranging from 0 concentration of antibiotic to 1000 ug per mol. Erythromycin and nalidixic acid were completely inhibitory at all concentrations of antibiotic. Growth occurred in the 0 concentration tube. There was no inhibition (at all concentrations) in the presence of penicillin suggesting that the forms do not have a cell wall (since the mode of action of penicillin is to inhibit cell wall synthesis of bacteria). Amphotericin B was not inhibitory.

The inhibition of growth by erythromycin and nalidixic acid suggest that these forms may be bacterial in origin.

EXAMPLE 4

Staining procedures. Stains used and results presented in table 2.

Acridine Orange Stain was used (according to methods by McCarthy and Senne, (1980) J. Clin. Microbiology, 11:281 (entire content incorporated herein by reference).

Results:

Young bodies stain orange; as they grow old they stain green.

Other stains were used according to the instructions of the manufacturor (Molecular Dynamics, Inc.)

"Syto-live™" procedure (generally): To perform the assay, calcein AM and ethidium homodimer are separately dissolved in fairly polar water miscible solvents, such as DMSO, DMF, ethanol, methanol, or acetonitrile to form a calcein AM stock solution and a ethidium homodimer stock solution. Solvents for calcein AM are limited by the tendency of calcein AM to hydrolyze in the presence of water. Preferably the reagents are dissolved in dry DMSO, usually about 5 mM calcein AM and about 12 mM ethidium homodimer, each in dry DMSO. Stock solutions should be protected from light and from prolonged exposure to room temperature. Preferably, the stock solutions are stored frozen in vials inside a plastic bag containing a desiccant.

Stock solutions of calcein AM and ethidium homodimer are diluted to form working solutions of calcein AM and ethidium homodimer. The working solution of calcein AM should be prepared shortly before use because calcein AM is sensitive to moisture and hydrolyses slowly in aqueous solution, leading to increasing levels of background fluorescence. Ethidium homodimer is more stable and relatively insensitive to moisture. To prepare working solutions, frozen stock solutions are allowed to thaw to room temperature. Optimal fluorescence measurements are obtained when the reagent concentrations are adjusted for a particular experimental system, i.e. cell type, cell number, dye concentration, temperature, incubation time, and detection system, e.g. fluorescence microscopy, fluorescence well-plate scanner, fluorometer or flow cytometry. Optimization experiments can be performed by separately treating live cells and dead cells with various dye concentrations. Each probe should be optimized separately. Reagent concentrations should be selected that permit a clear distinction between live and dead cells with either probe. Selection of filter sets, instrument sensitivity settings, and the number of cells per test may affect the optimization.

ICAPs disclosed by the present inventors stain green using "Syto-live™" or "BacLight™" staining.

EXAMPLE 5

Electron Microscopic Examination of ICAPs

Figure 2:
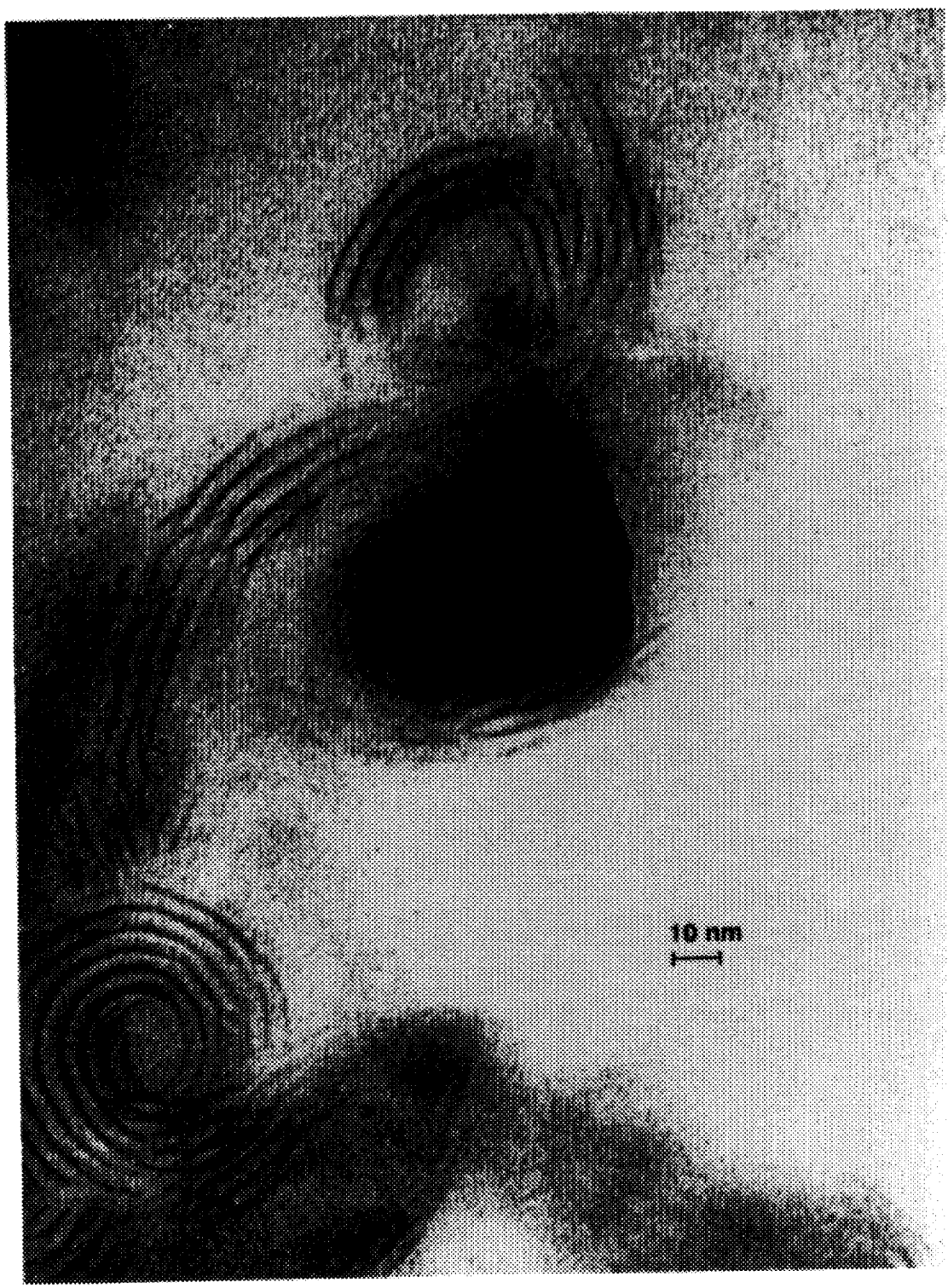
Figure 3:
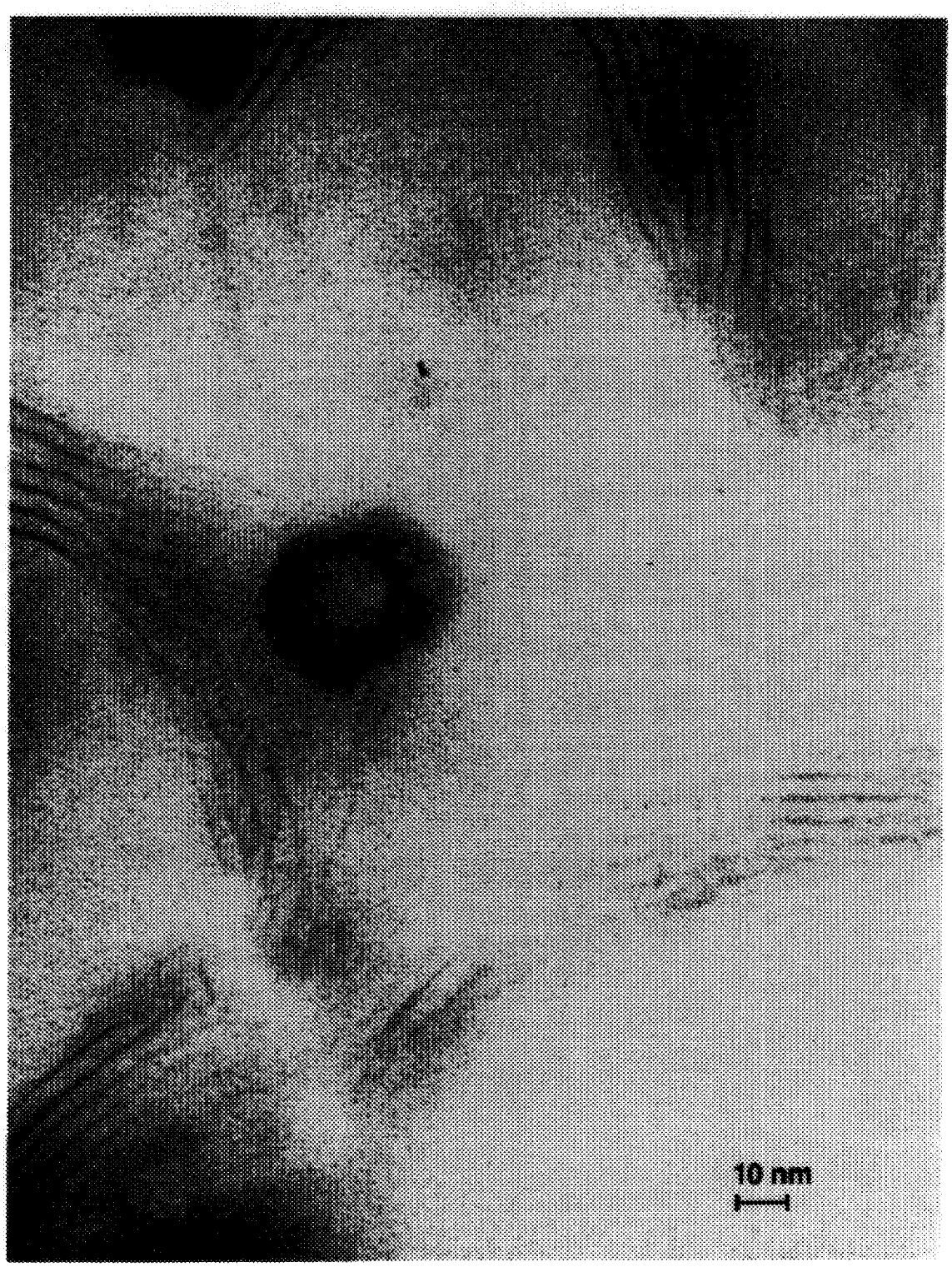

Electron Microscopy Methodology: The ICAPs were grown in 100% human serum from an interstitial cystitis patient and the forms were fixed in 3% gluteraldehyde containing 3% sucrose. These specimens were postfixed in 1% osmium tetroxide in 0.2M phosphate buffer pH 7.2 for 1 hours. They were then dehydrated in 50%, 70%, 80%, 90% and 100% alcohol for 30 minutes each; transferred to propylene oxide and 100% alcohol at 1:1 for 30 minutes, and at 100% propylene oxide for 30 minutes. The samples were put into 100% propylene and embedded in 812 epoxy at the following intervals: 4 hours at 1:1; 16 hours at 1:2; 8 hours at 1:3; and 24 hours at 100%. Lastly, the samples were transferred, reembedded in 812 epoxy and polymerized at 60° C. in the oven for 24 hours. Thin sections 50 to 70 nm were double stained with uranyl acetate and lead nitrate and photographed with a Zeiss 109 electron microscope and enlarged onto paper to final magnifications of 100 to 450 thousand. FIGS. 1–3 show electron micrographs of these preparations.

EXAMPLE 6

Antiserum Production

Rabbit Immunization Using Antigens Derived from a Human Serum Pool, and from the Serum of One IC-patient Animals used: Three female New Zealand White (NZW) rabbits about 4 months old weighing approximately 3.0 pounds.

Antigen source:
A. IC-62 serum

One ml of the patient's serum was filtered using a 0.2M filter and incubated at 35° C. for 22 days prior to immunization.

B. Human serum

Ten ml of commercially available (Whittaker) human serum pool was filtered using a 0.2µ filter and kept at 35° C. for 8 days prior to immunization.

ICAP preparation:
1. Two ml aliquots from the human serum cultures and one ml from the IC-62 serum culture were obtained and centrifuged at 8,000 rpm for 10 minutes.
2. ICAP pellets were washed 2× with a 10% sucrose solution.
3. After the last centrifugation, cell pellets were resuspended in 0.5 ml sterile water. All suspensions were plated on blood agar plates. No growth was reported after 48 hours.
4. Aliquots from the pooled human and IC-62 cultures were obtained and observed using phase contrast microscopy, X1000 magnification. Clusters of coccal forms and large round forms were recorded.

Antigen Preparation using Hunter's TiterMax™ Adjuvant

Using one ml syringe with an 18 gauge blunt needle, we prepared a 180 µl emulsion with each antigen: 80 µl "TiterMax™"+100 µl antigen Procedure:
1. Attach a blunt 18 gauge needle to a 1 ml plastic syringe.
2. Add 80 µl of "TiterMax™" adjuvant to the 1.5 ml centrifuge tube. Add 50 µl of the antigen solution.
3. Draw the antigen-adjuvant mixture into the syringe and back into the microcentrifuge tube several times until a thick white emulsion forms.
4. Add the remaining 50 µl of the antigen solution and repeat the process.
5. This is the final emulsion to be used to inject the animals. Emulsion was kept at −70° C. to be used for a booster at a later time.

| Rabbit immunization | | | |
|---|---|---|---|
| Antigen source | Injection route | Total Injections | Volume per injection Site |
| Human | IM | 2 | 40 µl Each hind leg |
| IC-62 | IM | 2 | 40 µl Each hind leg |

| Immunization schedule | | |
|---|---|---|
| Source | Primary Immunization | Booster |
| Human antigen | | 28 days from primary |
| IC-62 antigen | | 28 days from primary |

EXAMPLE 7

SDS PAGE Electrophoresis of Human ICAPs

A. Growing Cells
1. ICAPs cultivated from 100% serum cultures of pooled human sera from Whittaker, Inc. in 30 ml sterile bottles, as described in example.
2. After 60 days of incubation at 35° C. cells were centrifuged at 8,000 rpm for 15 minutes.
3. Cell pellets were washed 3 times with PBS and finally were resuspended in 4 ml of PBS.

B. Sonication

Cells were disrupted using a sonicator.

Disruption Procedure:
1. Cells were suspended in 4 ml of PBS in round bottom glass tubes.
2. Sonicator was turned on and set on power strenght 3.
3. Cells were sonicated at 12 seconds intervals.
4. Extreme care was taken in keeping the temperature at 40° C. in between sonications.
5. Cells were observed microscopically to determine degree of disruption.
6. Cells required a total of 25 sonication outputs in order to achieve 90% disruption.

C. Protein concentration was determined by Lowry assay. 300 µg/ml, volume approximately 5 ml.

D. The protein was concentrated with an "Amicon™" apparatus.

Final volume: 1 ml (concentrated approximately 5 fold). Protein 1.5 mg/ml

This experiment was repeated at least 3 times with substantially the same results.

This experiment was also performed using serum from presumed interstitial cystitis patients with similar results.

D. SDS-PAGE gel electrophoresis running conditions
Gel 12% acrylamide Tris-HCl
Sample buffer 0.5M Tris-HCl; 1% glycerol; 0.05% bromophenol blue;
0.2% SDS (10%) and 0.05% 2-β-mercapto ethanol
Running buffer Tris base, glycine, SDS
Loading volume 45 µl
Loading concentration 20 µg
Procedure:
1. Heat protein solution at 56° C. for 5 minutes.
2. Load each well with 45 µl of the protein solution in sample buffer.

3. Run the gel at 200 V. Running time was approximately 45 minutes.
4. After electrophoresis, the gel was stained for 30 minutes with Coomasie blue stain. Destaining was done overnight using 40% Methanol/10% Acetic acid.

SDS-PAGE Results:
Four bands were detected:
Human 30, 58, 69, 97.4 kilodaltons
Amersham "Rainbow™" molecular weight standards were used to calibrate the gel.

EXAMPLE 8

Immunofluorescence Assay

A. Slide test

We started testing the sera one week post immunization.
Procedure:
1. Human pool sera and IC patient serum were incubated at 35° C. for approximately one month.
2. Aliquots of 0.5 ml were centrifuged at 2,500 rpm for 10 min.
3. The sediment was then washed 2 times with 10% Sucrose solution.
4. After the final wash, the pellet was resuspended in 200 µl of 10% sucrose solution.
5. One drop of the cells-sucrose suspension is then placed on a fluorescent antibody slide (Clay Adams) and allowed to air dry.
6. The slides were fixed with 100% methanol.
7. 100 µl of rabbit serum is added to the slide undiluted and in a 1:100 dilution with FA buffer.
8. Slides were incubated in a moist chamber protected from direct light at 35° C. for 30 minutes.
9. Slides were then rinsed 2 times with FA buffer.
10. 100 µl of anti-rabbit IgG-FITC labelled conjugate diluted 1:160 was added to the slides.
11. Slides were incubated in a moist chamber as previously described.
12. Washing step as above.
13. Slides were read in a fluorescent microscope.

Results:
Pre-immune rabbit serum Negative.
Post-immunization (Weeks)
Post-immunization (Weeks) Fluoresence rated one + to four +.

| | |
|---|---|
| One | + |
| Two | + |
| Three | − |
| Four | − |
| Five | ++++ |
| Six | +++ |
| Seven | +++ |
| Eight | ++ |
| Nine | + |

EXAMPLE 9

Western Blot

Buffers and Solutions:
1. TBS (Tris, NaCl)
2. TTBS (TBS with 0.05% Tween-20)
3. Blocking Solution (3% gelatin in TBS)
4. Antibody buffer (1% gelatin in TTBS)
5. 1st antibody solution (1% gelatin in TTBS)
6. 2nd antibody solution (1% gelatin in TTBS)
7. Color development buffer-HRP developer preparation Procedure:
After the SDS PAGE, we blotted the gel into a nylon membrane using a Bio-Rad transblotting apparatus. Blotting was accomplished at 4° C. overnight at 20 constant voltage. After blotting different incubation and blocking steps were performed at room temperature with constant agitation using a rocker platform:
1. We soaked the nylon membrane in Ponceau solution for 5 minutes.
2. Rinsed the membrane with distilled water for 5 minutes until the bands became visible.
3. Rinsed the membrane with TBS for 10 minutes.
4. Added the blocking solution and incubated for 1 hr.
5. Washed with TTBS for 10 minutes with gentle agitation.
6. Added 1st antibody solution diluted 1:500 and incubated overnight with gentle agitation.
7. Washed the membrane 2× in TTBS for 5 min/wash.
8. Added the conjugate solution: Goat anti-rabbit IgG HRP diluted 1:3,000. Incubated for 2 hr at room temperature.
9. Washed 2× in TTBS for 5 min/wash at room temperature.
10. Washed 1× in TBS for 5 min.
11. Added the color developer solution and waited for the appearance of the bands.
12. After 15 minutes the bands became visible. We washed the membrane with distilled water for 5 min/wash to stop further development and to reduce the background.

Results:
Four bands were visible: 28, 58, 68 and 80 (kilodaltons).

Test Results for Assays Detecting the Presence or Amount of Anti-ICAP Antibody in a Test Sample The results of the ICAP test are interpreted as follows: if
(1) said patient has no symptoms of IC, then the presence of ICAP analyte indicates that the patient has a condition predisposing to IC;
(2) said patient has symptoms of IC, then the presence of said analyte indicates that the patient has IC;
(3) said patient has symptoms of IC, then the absence of said analyte indicates that the patient does not have IC.

The exemplary assays of the present invention typically involve the addition and incubation of several different reagents. A variety of different buffer and washing solutions can be used to stabilize the reagents and to remove excess reagents or test sample from the reaction. As is well-known to those skilled-in-the-art, modifications can be made in the buffer and washing solutions, as well as in the reaction times.

The assay reagents can also be provided in kit form. A test kit to detect ICAP analyte would typically contain a solid phase material upon which an ICAP capture binding member is immobilized and optionally include an appropriate supply of a suitable indicator reagent, buffers and washing solutions. Thus, a test kit to detect ICAP antigen would typically contain a solid phase material upon which anti-ICAP antibody is immobilized or upon which components of the patient's test sample can be immobilized (e.g., direct immobilization of the antigen upon the solid phase), and optionally include appropriate amounts of a suitable indicator reagent, buffers and washing solutions. Other components such as stabilizers and preservative agents can also be present in the kit and/or in the reagents. Likewise, a test kit to detect ICAP antigen would typically contain a solid phase material upon which ICAP antibody is immobilized and optionally include an appropriate supply of a suitable indicator reagent, buffers and wash solutions.

What is claimed is:

1. A process for obtaining an interstitial cystitis associated particle (ICAP), produced by the process of obtaining a test sample from a person having symptoms of interstitial cystitis, the test sample being selected from the group consisting of human body fluids, a first serum, a first plasma, and tissue; and filtering the test sample through a filter, the filter containing pores with a diameter less than or equal to approximately 0.22 mm; and propagating the test sample in enriched cell free medium effective for growing an interstitial cystitis associated particle; and identifying a particle by an effective means, the particle having a core with a diameter of approximately 40–80 nm, the core having sheets continuing therefrom, and the sheets being regularly spaced apart.

2. The process of claim 1, wherein the the enriched cell-free medium is substantially free of antibiotics except antibiotics selected from the group consisting of polyene antibiotics and β lactam antibiotics.

3. The process of claim 1, wherein the medium comprises blood components chosen from the group consisting of the first serum, the first plasma, a second serum or a second plasma.

4. The process of claim 1, wherein the incubation is for a period of 1 to 6 weeks.

5. The process of claim 1, wherein the ICAP is obtained by disrupting the test sample sufficiently to release components therefrom.

6. The process of claim 5, wherein the components are sorted into an ordered array.

7. The process of claim 5, wherein the components are contacted with specific antibodies, whereby immune complexes are formed.

8. A diagnostic assay for interstitial cystitis, the diagnostic assay comprising the process of providing a test sample from a human having the symptoms of interstitial cystitis;

the samples being selected from the group consisting of human body fluids, serum, plasma, and tissue; and filtering the samples through a filter containing pores with a diameter less than or equal to approximately 0.22 mm; and collecting the filtrates; and disrupting the filtrates sufficiently to release components therefrom; and sorting the components into an ordered array; and contacting the components with interstitial cystitis associated particle specific antibodies sufficiently to form immune complexes with the specific antibodies, and wherein the components that form the immune complexes have molecular weights of approximately 28, 58, 68, and 80 kilodaltons; and detecting the immune complexes by an effective means, whereby a distribution pattern of the immune complexes is produced.

* * * * *